United States Patent [19]

Sleeter et al.

[11] Patent Number: 4,663,015
[45] Date of Patent: May 5, 1987

[54] ELECTROPHORESIS APPARATUS FOR NUCLEIC ACID SEQUENCING

[75] Inventors: Donald D. Sleeter, Berkeley; Raymond D. von Alven, San Rafael; George G. Fernwood, San Anselmo, all of Calif.

[73] Assignee: Bio-Rad Laboratories, Inc., Richmond, Calif.

[21] Appl. No.: 782,756

[22] Filed: Sep. 30, 1985

[51] Int. Cl.⁴ .............................................. B01D 13/02
[52] U.S. Cl. .............................. 204/299 R; 204/182.8
[58] Field of Search ......................... 204/299 R, 182.8

[56] References Cited

U.S. PATENT DOCUMENTS

| | | | |
|---|---|---|---|
| 4,337,131 | 6/1982 | Vesterberg | 204/299 R X |
| 4,339,327 | 7/1982 | Tyler | 204/299 R |
| 4,518,476 | 5/1985 | Delony et al. | 204/299 R |
| 4,560,459 | 12/1985 | Hoefer | 204/182.8 |
| 4,574,040 | 3/1986 | Delony et al. | 204/299 R |

*Primary Examiner*—John F. Niebling
*Attorney, Agent, or Firm*—Townsend and Townsend

[57] ABSTRACT

An integrated plate structure provides a novel component for use in an electrophoretic sequencing cell. The integrated plate structure consists of a glass plate and a plastic plate bonded together along a raised edge of the latter, the edge extending along the sides and bottom of the plastic plate. The plates thus form a permanent enclosure for an upper buffer solution, open at the top for filling. The glass plate further serves as one of the two glass plates forming the gel enclosure.

14 Claims, 10 Drawing Figures

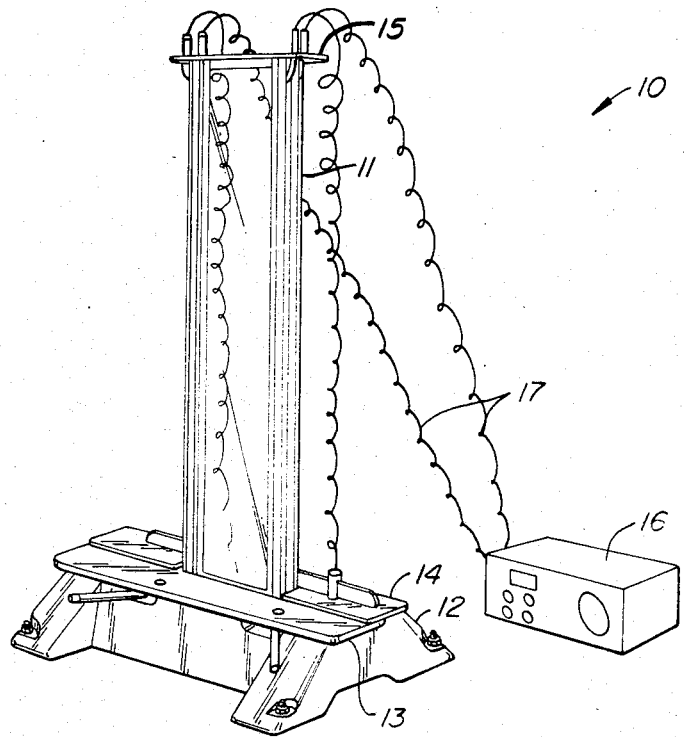
Fig._1.
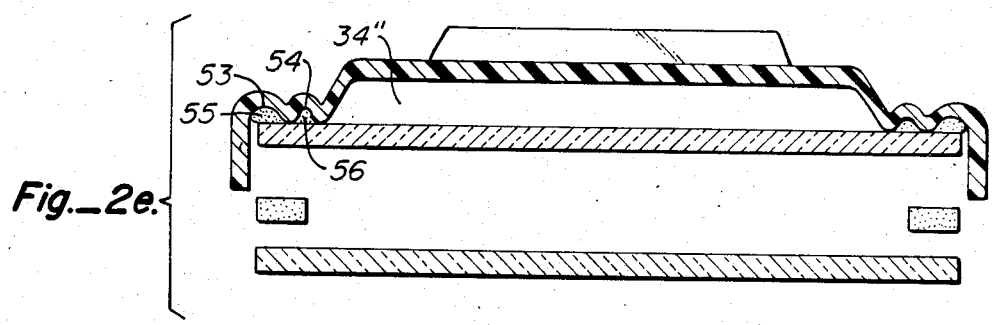
Fig._2e.

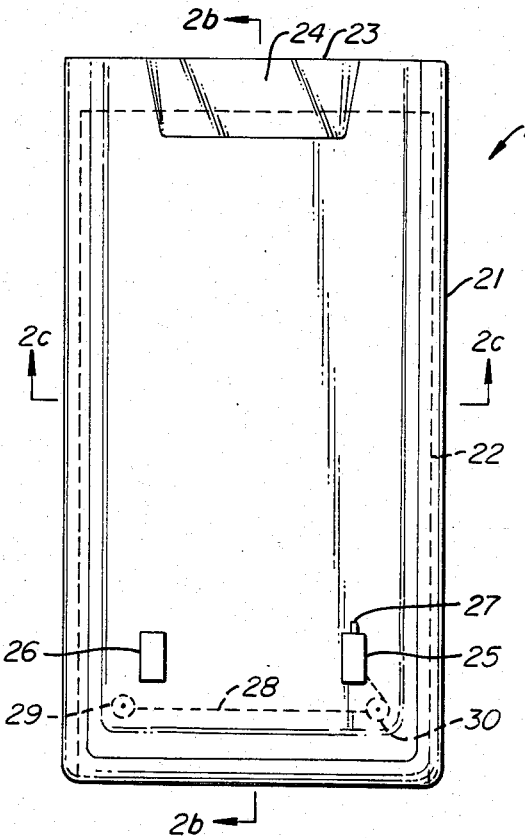
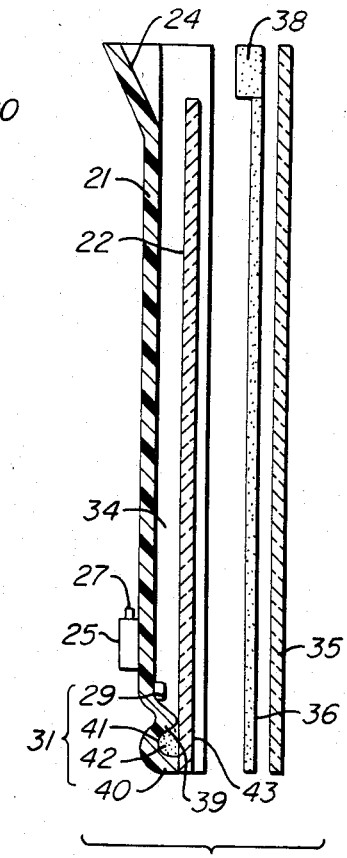
Fig._2a.
Fig._2b.
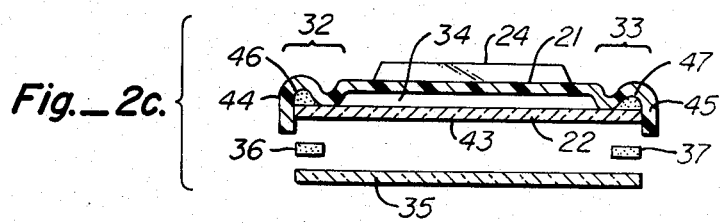
Fig._2c.
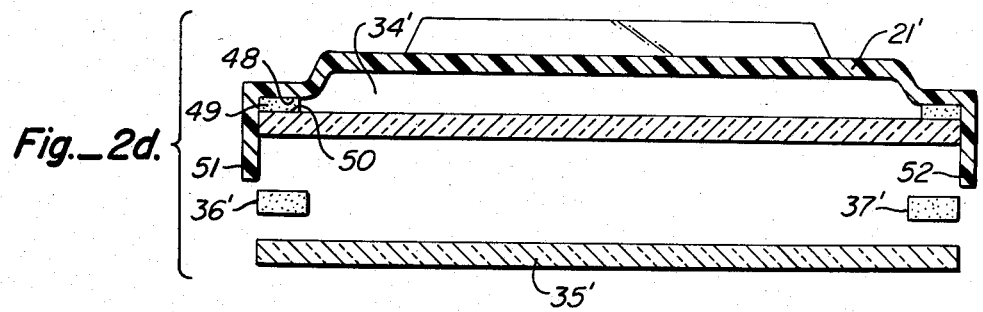
Fig._2d.

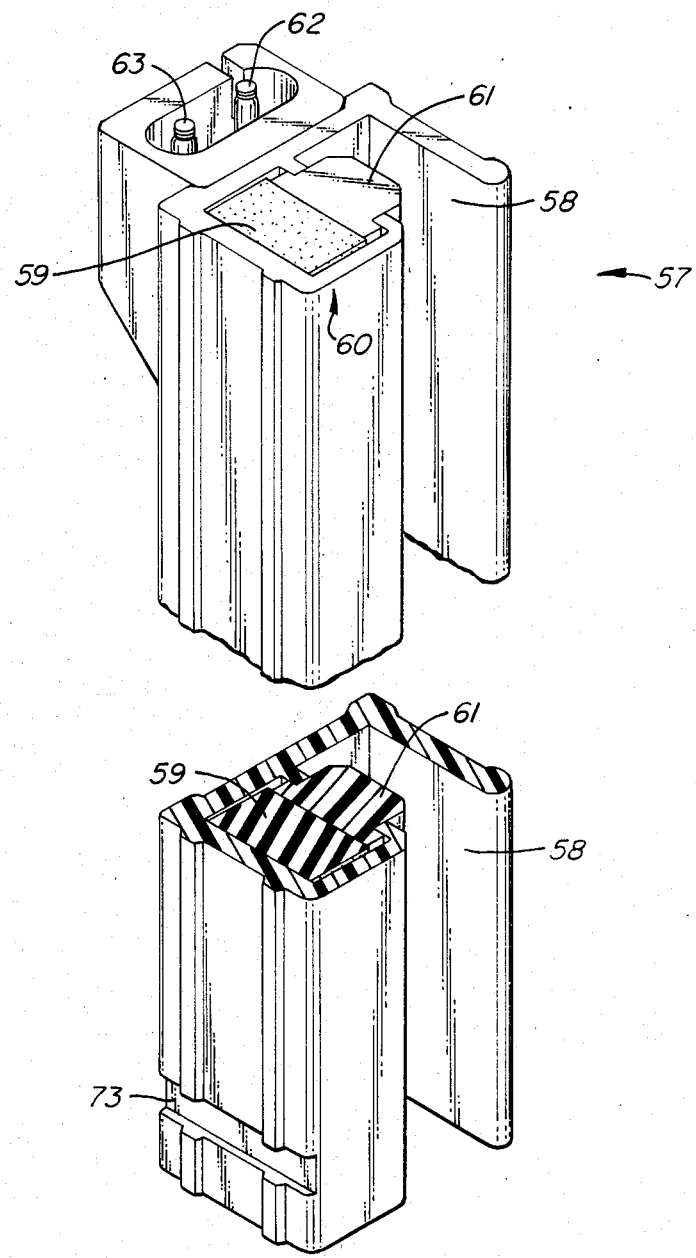
Fig._3.

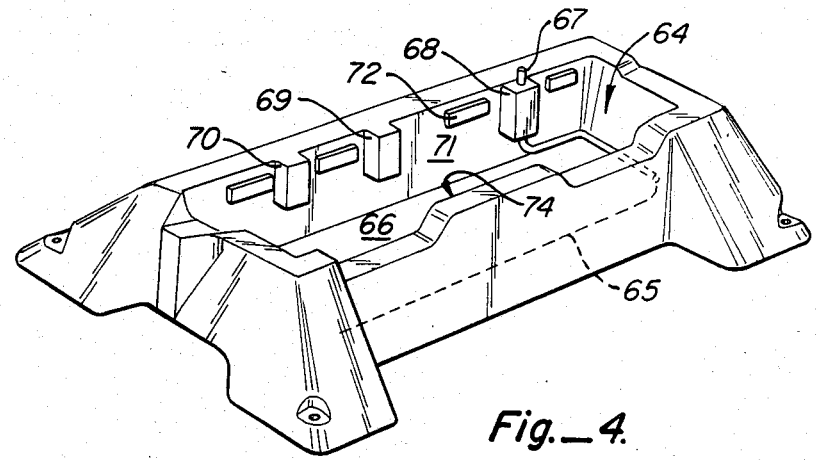
Fig._4.
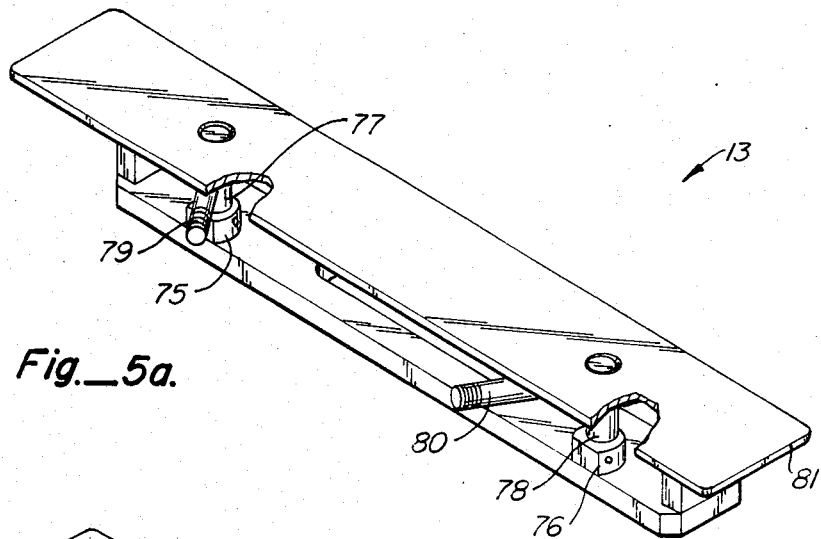
Fig._5a.
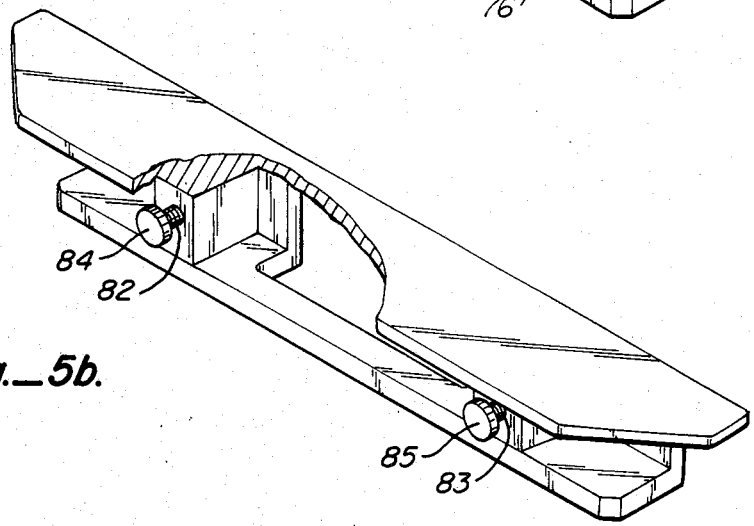
Fig._5b.

ELECTROPHORESIS APPARATUS FOR NUCLEIC ACID SEQUENCING

BACKGROUND OF THE INVENTION

This invention relates to vertical slab gel electrophoresis systems, and in particular systems using gels of exceptional thinness and length, as needed to provide maximum resolution in the separation of nucleic acid fragments for sequencing purposes.

The difficulty of resolving nucleic acid fragments by electrophoresis has led to sequencing cell designs which are awkward to handle, susceptible to breakage and leakage, and potentially dangerous due to inadvertent mishandling. As in other electrophoretic techniques, the gels are cast and used in a sandwich-type arrangement between two flat glass plates separated by spacer strips along opposing side edges. The two plates are of unequal height, and a third plate, generally of plastic material, is placed on the outer side of the shorter glass plate with appropriate spacers along the sides and bottom to form a vertical compartment for an electrode buffer solution. The plastic plate extends above the top edge of the shorter glass plate so that the top edge of the gel slab will be immersed in the electrode buffer solution. The plastic plate and the two glass plates are clamped together along the side edges, with an intermediary greased rubber gasket along the sides and bottom of the plastic plate to prevent leakage of the buffer solution. Among the many disadvantages of such a system are the large number of pieces to be assembled, the awkwardness of obtaining proper alignment of the various plates and spacers, and the possible contamination of the buffer solution and consequently the gel itself by the grease needed to form a liquid-tight seal.

The need to overcome these problems and thereby improve the reliability of the equipment as well as provide for rapid assembly and disassembly of the parts is thus apparent. Accordingly, the present invention has been developed with these problems in mind and possibly others encountered in connection with the existing equipment.

SUMMARY OF THE INVENTION

An integrated plate structure for use as an upper buffer chamber in an electrophoretic sequencing cell is provided. The structure consists of one of the flat glass plates used to form the gel sandwich, plus the plastic plate described above. The two plates are bonded together along a raised edge which runs along the sides and bottom of the plastic plate, thereby forming a permanent enclosure, open at the top, for containing the upper buffer solution.

In one embodiment, the raised edge of the plastic plate contains a pair of parallel ridges with a curved valley in between. The valley is filled with an adhesive elastomer such as silicone rubber. When the edge of the glass plate is placed over the ridges, the elastomer bonds the plate together. On the exposed side of the plastic plate, the under surface of the valley forms a curved ridge over which the end clamps holding the gel sandwich together are fastened. The curvature of the ridge renders it capable of yielding under the pressure of the end clamps, thus lessening the tendency of the glass to break under the strain of the clamps. The curvature of the ridge further provides the plastic with a wide latitude of expansion and contraction. This helps the structure accommodate the thermal expansion caused by joule heating when the cell is in use, without causing undue strain on the glass.

In another embodiment, the raised edge contains a flat surface facing the glass plate, the two being separated by a resilient pad bonded to each. In addition to yielding under end clamp pressure, the pad undergoes shearing deformation to accommodate the differential in the rates of lateral thermal expansion of the glass and plastic plates which occurs under joule heating conditions.

In preferred embodiments, a further raised edge extends forward from the outer boundary of the raised edge described above, along each of the two side edges of the plastic plate, passing over the corresponding edge of the glass plate and a short distance beyond. This provides protection for the glass plate and also serves as a guide for the spacers and the other glass plate used to enclose the gel.

BRIEF DESCRIPTION OF THE DRAWINGS

FIG. 1 is a perspective view of an electrophoretic sequencing system incorporating the novel features of the present invention, as an illustrative embodiment thereof.

FIG. 2a is a rear elevation view of an integrated plate structure forming an upper buffer chamber and one side of a slab gel enclosure, the structure being one of the components of the system shown in FIG. 1.

FIG. 2b is a side cutaway view taken along line 2b—2b of FIG. 2a, 1 plus spacers and an additional glass plate used to form the gel enclosure, shown in exploded arrangement.

FIG. 2c is a cutaway view along line 2c—2c of FIG. 2a, further including the same spacers and glass plate shown in FIG. 2b.

FIG. 2d is a cutaway view of an alternative embodiment, corresponding to the view shown in FIG. 2c.

FIG. 2e is a cutaway view of a second alternative embodiment, again corresponding to the view shown in FIG. 2c.

FIG. 3 is a fragmented perspective view an end clamp for holding the various plates forming the gel enclosure of FIGS. 1, 2a, 2b and 2c together.

FIG. 4 is a perspective view of the base shown in FIG. 1, which retains a lower buffer solution and supports a gel enclosure. Locking features included in one embodiment of the present invention are incorporated into the base.

FIG. 5a is a perspective view in partial cutaway of a base clamp, one of the components of the system shown in FIG. 1, for stabilizing the gel enclosure in the base.

FIG. 5b is a perspective view in partial cutaway of an alternative base clamp, designed to provide a function equivalent to that of the clamp of FIG. 5a.

DETAILED DESCRIPTION OF THE PREFERRED EMBODIMENTS

To demonstrate the functions and interrelationships of the various components and features comprising the novel aspects of the present invention, a complete electrophoretic system in accordance with the present invention is shown in FIG. 1.

The figure depicts a vertical electrophoresis apparatus 10 consisting of a series of components, including a gel enclosure 11 capable of holding an elongate slab gel and incorporating in its structure a compartment for an upper buffer solution; a hollow base 12 for retaining a lower buffer solution and receiving the lower end of the gel enclosure 11 beneath the liquid level; a lever-operated clamp 13 inserted into the hollow base 12 for stabilizing the gel enclosure by forcing it backwards against the inner rear wall of the base; safety plates 14, 15 to enclose the remainder of the base and the top edge of the gel enclosure, respectively; and a power supply 16 and associated electrical lines 17 for electrifying the two buffer solutions. Samples to be separated are placed at the upper edge of the gel, and migration of the components occurs downward under the influence of the electric current caused by the power supply.

The integrated plate structure 20 forming the upper buffer chamber is seen in FIG. 2a. The structure consists of a plastic plate 21 and a glass plate 22 bonded together. The plastic plate 21 is forward in the view shown. The plates are generally rectangular in shape, and of unequal height, the glass plate being shorter.

A central portion 23 of the top edge of the plastic plate 21 is flared away from the glass plate to provide an angled slot 24. The slot facilitates the insertion of a comb into the gel solution prior to casting to form sample wells, and also facilitates the insertion of samples into the wells, and the addition of upper buffer solution into the volume between the plastic plate 21 and the glass plate 22.

Toward the lower end of the plastic plate are a pair of blocks 25, 26, extending outward. One of these blocks mates with a corresponding block inside the base 12 of FIG. 1 to serve as alignment guides for placement of the gel enclosure inside the base. The mating blocks inside the base are described in more detail below in connection with FIG. 4.

The rightmost block 25 in the view shown in FIG. 2a also serves as a support for an electrical connection through which power made be supplied to the electrode buffer solution residing in the space beween the plastic and glass plates (21, 22). The connection shown is a banana plug 27. The plug leads to an exposed electrode 28 running along the inner side of the plastic plate 21 and extending horizontally along a major portion of the width thereof, supported by a pair of pegs 29, 30. To supply power to the electrode 28, an electric line from the power supply 16 (FIG. 1) is placed in engagement with the banana plug 27, as shown in FIG. 1.

It may be seen in FIGS. 2b and 2c that the bottom edge 31 and the two side edges 32, 33 of the plastic plate 21 are raised in the direction of the glass plate 22 to define an interior space 34 between the two plates, the space being open at the top and closed at the bottom and sides and thereby capable of retaining a buffer solution. Also shown in FIGS. 2b and 2c are a separate glass plate 35 and a pair of spacer strips 36, 37 which, together with the first-mentioned glass plate 22, form a space for retaining a slab gel. The outer glass plate 35, like the plastic plate 21, extends above the upper edge of the inner glass plate 22. Since the gel extends only as high as the inner glass plate 22, the upper buffer solution retained in the interior space 34 between the inner glass plate and plastic plate may have a liquid level above the upper edge of the gel, thereby immersing the gel. A pair of spacer blocks 38 thicker than the glass plate laterally seal off the volume above the upper edge of the inner glass plate 22 to prevent lateral leakage of the upper buffer solution. The spacer blocks 38 are preferably closed cell foam pads.

In the embodiment shown in FIG. 2b, the raised edges have an undulated cross-section, forming a pair of parallel ridges 39, 40 with a curved valley 41 in between. The valley 41 is filled with an adhesive material 42, preferably an elastomer such as silicone rubber, capable of binding the plastic to glass. It is preferable that a resilient elastomer be used, which will yield to any distortion of the curvature of the plastic which might occur due to temperature fluctuations arising from joule heating generated by the current passing through the electrode 28. It has been found that this minimizes the stress on the inner glass plate 22 and lessens the tendency toward breakage or leakage.

In the embodiment shown, the outer ridge 40 is coterminous with the lower edge of the glass plate 22, permitting full access of the gel situated between the two glass plates to the lower buffer solution. As an alternative, the outer ridge 40 may pass over the edge of the glass plate, provided that it does not extend beyond the opposing surface 43.

As evident in the horizontal cross-section of FIG. 2c, the outer ridges 44, 45 pass over the side edges of the glass plate 22 and extend a short distance forward in the direction of the spacers 36, 37 and detached glass plate 35. These ridges thus form an extension of the plastic plate 21, serving as both a guide and a protective shield for the spacers 36, 37 and outer glass plate 35. Alignment of all parts is thereby facilitated.

The side edges have an undulated cross-section defining curved valleys 46, 47 for the adhesive in a manner similar to the bottom edge shown in FIG. 2b.

An alternative embodiment is shown in FIG. 2d, where the raised edge forms a flat surface 48 rather than the curved valley 46 of the embodiment of FIG. 2c. The resilient elastomer of FIG. 2c is replaced by a pad 49 of fluid-impermeable resilient material. The pad 49 is interposed between the flat surface 48 and the glass plate 22' and bonded to each along the opposing surfaces 48 and 50. The flat surface 48 and the pad 49 each extend the full length of the sides and bottom of the integrated plate structure (i.e., three of its four sides) to provide a liquid retaining space 34' between the plastic plate 21' and the glass plate 22', open at the top, as in the first embodiment. By virtue of its thickness, which in most applications will be from about 1 to about 10 mm, and its resilient deformable character, the pad 49 undergoes a shearing deformation when the plastic and glass plates expand at the elevated temperatures caused by joule heating of the apparatus during electrophoresis. Being of different materials with different coefficients of thermal expansion, the plastic and glass plates will extend laterally to different lengths, the two surfaces 48 and 50 moving relative to each other. The deformable character of the pad 49 permits it to retain both its adhesion to the two surfaces and its liquid retaining ability.

The pad 49 may be any material having the above characteristics. Examples are silicone rubber and polyurethane foam. Likewise, the adhesive material bonding the pad to the plastic and glass surfaces may be any material, preferably flexible, which is capable of holding a water-tight bond at the elevated temperatures and shearing strains which may be encountered during the use of the apparatus. Examples of such material are silicone adhesive and acrylic adhesive.

The embodiment of FIG. 2d contains further raised edges 51, 52 which pass over the side edges of the glass plate 22' and extend a short distance forward toward the spacers 36', 37' and the detached glass plate 35'. These raised edges 51, 52 serve the same functions as the outer ridges 44, 45 of the embodiment of FIG. 2c.

A second alternative embodiment is shown in FIG. 2e, where the raised edge forms a pair of parallel curved valleys 53, 54. The outer valley 53 is filled with adhesive 55, preferably a resilient elastomer, corresponding to the adhesive in FIG. 2c. The inner valley 54 retains a resilient cord 56 of fluid-retaining material such as foam rubber or a plastic foam. The cord serves as a gasket to prevent seepage of the elastomer into the interior space 34″ between the glass and plastic plates.

FIG. 3 depicts one of the two end clamps 57 which fasten over the vertical side edges of the gel enclosure, fitting over the edge of the outer glass plate 35 and the back side of the raised edge of the plastic plate 21, whether it be curved as in the embodiments of FIGS. 2c and 2e or flat as in the embodiment of FIG. 2d. The tension of the clamp is thereby restricted to the region of the curvature of the plastic plate and the adhesive material in the first embodiment or the region of the resilient pad in the second embodiment. Although shown with a center section removed, the clamp is continuous and contains a recess 58 extending its full length for receiving the vertical edge of the gel enclosure. Clamping pressure is maintained by a deformable cushion 59 of elastomeric material retained in the clamp body 60, and transmitted through a rigid bar 61 along which the gel sandwich can be slid.

Incorporated into the end clamp structure are a pair of banana plugs 62, 63 connected by a metallic strap (not shown). These plugs and the metallic strap connecting them, as well as a similar combination on the opposing end clamp, serve to complete the circuit supplying power to the electrodes and the buffer solutions when all parts are assembled. Referring to FIG. 1, it may be seen that cables from the power supply and the electrodes terminate at the upper safety plate 15, where they are separated by a gap. The gap is bridged by the two banana plugs 62, 63 and the connecting lead between them (not shown) only when the upper safety plate 15 is in place. This is a safety feature which prevents the inadvertent exposure of an electrified upper buffer solution when the upper safety plate 15 is removed from the assembly.

FIG. 4 provides a view of a hollow base 12 used to support the gel enclosure and the lower buffer solution. The base contains a recess 64 which functions as the lower buffer chamber. An electrode 65 runs along the floor 66 of the recess, leading to a banana plug 67 for connection to the external power supply (FIG. 1). The banana plug extends from a block 68 mounted on the inner rear wall 71 of the recess. A further block 69 serves as a guide for the positioning of the block 25 located on the rear of the plastic panel of the gel enclosure (see FIG. 2a) when the parts are assembled. When a wider gel enclosure is used, a still further block 70 serves as a guide for the similar positioning of a corresponding block on the wider plastic panel.

Also extending from the inner rear wall 71 of the recess 64 are a series of projections 72. Returning to FIG. 3, it may be seen that corresponding indentations 73 are formed toward the lower end of each end clamp 57. The projections and indentations are adapted to mate with each other when the end clamps are forced against the rear wall 71, thereby preventing vertical movement of the end clamps and hence the gel enclosure with respect to the base. In alternative arrangements, the projections and indentations may be reversed, so that the former are on the end clamps and the latter are in the rear inner wall of the base recess. The arrangement shown, however, is preferred.

In general, the shape, configuration, and placement of the projections and indentations may vary widely. A particularly convenient structure, however, is that shown in the drawing, i.e., where the projections are elongate, horizontal rectangular blocks or tongues, and the indentations are horizontal grooves. It is further preferred that more than two such projections be included, as shown, to accommodate a variety of gel enclosures of different widths.

FIG. 5a depicts in detail the base clamp 13 which stabilizes the gel enclosure in the vertical position inside the base. The clamp is designed to be inserted in the recess 64 of the base, between the inner front wall of the recess 74 (FIG. 4) and the front of the gel enclosure 11 (FIG. 1). Upon tightening, the clamp is expanded between these two surfaces, forcing the gel enclosure against the rear wall. Expansion is achieved by a pair of cams 75, 76 mounted on shafts 77, 78, which are in turn rotated by levers 79, 80. As the levers are turned, the cams press against the inner front wall 70 of the recess (FIG. 4), urging the body 81 of the clamp backwards against the gel enclosure. The clamping force secures the projections 72 and indentations 73 in engagement with each other, so that the gel enclosure cannot be lifted out of the base until the clamp is loosened. Adjustable screws may be substituted for the cams, as may a variety of other similar structures.

An alternative base clamp is shown in FIG. 5b. Here, expansion is achieved by a pair of screws 82, 83 with flat heads 84, 85 having knurled edges to permit finger turning. The screws are adjusted prior to placement of the clamp in the recess of the base, so that the flat screw heads 84, 85 press against the inner front wall 70 of the recess (FIG. 4) when the parts are assembled, forming a tight fit. Otherwise, the clamp is similar in function and use to that of FIG. 5a.

The foregoing description is offered for illustrative purposes only. Numerous modifications, variations, and further embodiments beyond those described herein will be readily apparent to those skilled in the art, while still falling within the spirit and scope of the invention as claimed hereinbelow.

What is claimed is:

1. Apparatus serving as a combination gel enclosure and upper buffer chamber for use in vertical gel slab electrophoresis, said apparatus comprising:
   a first glass plate;
   a second glass plate adapted to cooperate with said first glass plate to form a gel slab retaining space on one side of said second glass plate when assembled;
   a fluid-impermeable resilient material interposed between said raised edge of said plastic plate and said second glass plate;
   an exposed electrode inside said liquid retaining space;
   a plastic plate having a raised edge extending along a portion of the periphery thereof, said plastic plate being bonded to the other side of said second glass plate along said raised edge to define a liquid retaining space between said plastic plate and said second glass plate; and
   a fluid-impermeable resilient material interposed between said raised edge of said plastic plate and said second glass plate.

2. Apparatus in accordance with claim 1 in which said first and second glass plates and said plastic plate are substantially rectangular and said first and second glass plates are of approximately equal width.

3. Apparatus in accordance with claim 1 in which at least a central portion of said second glass plate is of lesser height than both said first glass plate and said plastic plate when said plates are vertically disposed.

4. Apparatus in accordance with claim 1 further comprising a pair of liquid-retaining spacers capable of forming a lateral enclosure for a slab gel when placed between said first and second glass plates.

5. Apparatus in accordance with claim 1 further comprising an exposed electrode inside said liquid retaining space.

6. Apparatus serving as a gel enclosure and upper buffer chamber for use in vertical gel slab electrophoresis, said apparatus comprising:
a first flat glass plate which is substantially rectangular;
a second flat glass plate which is substantially rectangular and of lesser length than said first flat glass plate, adapted to cooperate with said first glass plate to form a gel slab retaining space on one side of said second glass plate when assembled;
a pair of liquid-retaining spacers extending the length of said second flat glass plate;
a plastic plate of substantially rectangular shape and having a raised edge extending along the bottom and sides thereof, said plastic plate being bonded to the other side of said second flat glass plate along said raised edge to define a liquid retaining space between said plastic plate and said second flat glass plate;
a fluid-impermeable resilient material interposed between said raised edge of said plastic plate and said second glass plate; and
an exposed electrode inside said liquid retaining space.

7. Apparatus in accordance with claim 1 in which said raised edge is comprised of a pair of ridges running parallel to said periphery with a curved valley in between said ridges, and said fluid-impermeable resilient material is an adhesive material filling said valley and bonding said glass to said plastic.

8. Apparatus in accordance with claim 7 in which said adhesive material is a fluid-tight cement.

9. Apparatus in accordance with claim 7 in which said adhesive material is an elastomer.

10. Apparatus in accordance with claim 7 in which the outermost ridge of said pair of ridges passes over the side edges of said second glass plate and extends beyond said second glass plate to form guides for placement of said first glass plate.

11. Apparatus in accordance with claim 1 in which said raised edge includes a flat surface facing said second glass plate, and said fluid-impermeable resilient material is a fluid-impermeable resilient pad interposed between and bonded to both said flat surface and said second glass plate.

12. Apparatus in accordance with claim 11 further comprising a second raised edge along the outer boundary of a portion of said flat surface, extending beyond said fluid-impermeable resilient pad and said second glass plate to form a guide for placement of said first glass plate.

13. Apparatus in accordance with claim 1 in which a portion of the periphery of said plastic plate over which said raised edge does not extend is flared away from said second flat glass plate.

14. A combination gel enclosure and upper buffer chamber for vertical gel slab electrophoresis, comprising:
a first flat glass plate of substantially rectangular shape;
a second flat glass plate of substantially rectangular shape and of lesser length than said first flat glass plate, adapted to cooperate with said first glass plate to form a gel slab retaining space on one side of said second glass plate when assembled;
a pair of liquid-retaining spacers extending the length of said second flat glass plate;
a plastic plate of substantially rectangular shape and of approximately the same length as said first flat glass plate, said plastic plate having a first raised edge extending along three sides thereof, said first raised edge including a flat surface facing said second flat glass plate;
a fluid permeable resilient pad extending the length of said flat surface, interposed between and bonded to both said flat surface and the other side of said second flat glass plate; and
said plastic plate further having second and third raised edges along two of said three sides parallel to one another, extending beyond said second flat glass plate to form guides for placement of said first flat glass plate, and a central portion along the fourth side thereof which is flared away from said second flat glass plate.

* * * * *